United States Patent
Zalevsky et al.

(10) Patent No.: US 11,406,294 B2
(45) Date of Patent: Aug. 9, 2022

(54) SYSTEM AND METHOD FOR IMPROVED MONITORING OF A SAMPLE

(71) Applicant: CONTINUSE BIOMETRICS LTD., Tel Aviv (IL)

(72) Inventors: Zeev Zalevsky, Rosh HaAyin (IL); Javier Garcia, Valencia (ES); Nisim Nisan Ozana, Rehovot (IL)

(73) Assignee: ContinUse Biometrics Ltd., Tel Aviv (IL)

( * ) Notice: Subject to any disclaimer, the term of this patent is extended or adjusted under 35 U.S.C. 154(b) by 648 days.

(21) Appl. No.: 16/347,921

(22) PCT Filed: Nov. 6, 2017

(86) PCT No.: PCT/IL2017/051207
§ 371 (c)(1),
(2) Date: May 7, 2019

(87) PCT Pub. No.: WO2018/087751
PCT Pub. Date: May 17, 2018

(65) Prior Publication Data
US 2019/0274602 A1  Sep. 12, 2019

Related U.S. Application Data

(60) Provisional application No. 62/420,161, filed on Nov. 10, 2016.

(51) Int. Cl.
*A61B 5/145* (2006.01)
*A61B 5/00* (2006.01)
*A61B 5/1455* (2006.01)

(52) U.S. Cl.
CPC ........ *A61B 5/14532* (2013.01); *A61B 5/0066* (2013.01); *A61B 5/0077* (2013.01); *A61B 5/14551* (2013.01)

(58) Field of Classification Search
CPC ....... A61B 5/145; A61B 5/00; A61B 5/14532; A61B 5/14551; A61B 5/0066; A61B 5/0077; A61B 5/14558
See application file for complete search history.

(56) References Cited

U.S. PATENT DOCUMENTS

| 5,212,667 A | 5/1993 | Tomlinson, Jr. |
| 8,638,991 B2 | 1/2014 | Zalevsky et al. |

(Continued)

OTHER PUBLICATIONS

Ozana, et al., Improved noncontact optical sensor for detection of glucose concentration and indication of dehydration level, Biomedical Optics Express, May 2014, pp. 1926-1940, vol. 5, No. 6.

(Continued)

*Primary Examiner* — Eric J Messersmith
(74) *Attorney, Agent, or Firm* — Browdy and Neimark, P.L.L.C.

(57) ABSTRACT

A system for use in monitoring one or more parameters of a subject's body is described. The system comprising: an illumination unit configured for providing pulsed coherent illumination and directing said illumination onto an inspected region on said subject's body; a collection unit configured for collecting light returning from said inspection region and generate a plurality of data pieces associated with secondary speckle patterns in said light; an external field stimulation unit configured for selectively generating external field stimulation onto the subject's body; and a control unit. The control unit is configured and operable for operating said illumination unit said collection unit and said external field stimulation unit and for receiving said plurality of data pieces from said collection unit to thereby determine said one or more conditions of the subject's body.

14 Claims, 2 Drawing Sheets

(56) References Cited

U.S. PATENT DOCUMENTS

| | | | |
|---|---|---|---|
| 9,668,672 B2 | 6/2017 | Zalevsky et al. | |
| 2001/0031914 A1* | 10/2001 | Gobeli | A61B 5/14558 |
| | | | 600/318 |
| 2002/0118903 A1 | 8/2002 | Cottrell et al. | |
| 2005/0171415 A1* | 8/2005 | Hirao | A61B 5/14558 |
| | | | 600/316 |
| 2006/0025659 A1 | 2/2006 | Kiguchi et al. | |
| 2012/0150014 A1 | 6/2012 | Metzger | |
| 2014/0058226 A1* | 2/2014 | Chernobrod | A61B 5/14532 |
| | | | 600/316 |
| 2014/0148658 A1* | 5/2014 | Zalevsky | A61B 3/16 |
| | | | 600/301 |
| 2016/0338623 A1* | 11/2016 | Tholl | A61B 5/1455 |

OTHER PUBLICATIONS

Ozana, et al., Noncontact speckle-based optical sensor for detection of glucose concentration using magneto-optic effect, Journal of Biomedical Optics, Jun. 2016, pp. 065001-1-065001-6, vol. 21(6).

Ozana, et al, Remote photonic sensing of glucose concentration via analysis of time varied speckle patterns, Advanced Materials Letters, 2018, pp. 624-628, vol. 9(9).

* cited by examiner

SYSTEM AND METHOD FOR IMPROVED MONITORING OF A SAMPLE

TECHNOLOGICAL FIELD

The present invention relates to system and method for monitoring of biological parameters and may relate in particular to non-invasive measurement of glucose blood level.

BACKGROUND

The human body contains many fluids carrying colloids or other solvents having vital functions within the body. For example, blood flowing in the circulatory system delivers necessary substances such as nutrients and oxygen to cells, and transports metabolic waste products away from those cells.

Some properties measurable via these bodily fluids are known to be indicative of different conditions of the person's body. Accordingly physiological and medical parameters of a subject may be determined in accordance with data on existence and concentration of selected materials in bodily fluids, enabling efficient monitoring the person's health condition. For example, the blood glucose level (also referred to as blood glucose concentration) may provide indication relating to malfunction of the digestive system, such as diabetes mellitus. The blood glucose levels are considered normal within certain range, while higher or lower levels can indicate abnormal condition that might be life threatening and typically requires treatment. Patients with diabetes mellitus may be needed to monitor their glucose levels routinely to verify desired glucose range in order to maintain their health. Additional blood content parameter may include oxygen levels, alcohol levels etc.

Generally, many non-invasive techniques have been devised in the field of measuring blood-related parameters, such as glucose level and oxygen saturation. Such techniques include impedance-based as well as optical measurement techniques. For example, some glucose measurement techniques are based on near infrared spectroscopy. In such techniques, a tissue is illuminated with light in the infrared spectrum, and the light reflected by the tissue and/or the light transmitted through the tissue is measured. The portion of light that is reflected and/or transmitted is indicative of the blood glucose level. Such glucose measurement techniques are used for tissue investigation in different depths varying from 1 to 100 millimeters or 10 to 50 micrometers. Additional glucose measurement techniques use Raman spectroscopy to measure scattered light that has been influenced by the oscillation and rotation caused by glucose. Glucose meters based on photo-acoustic spectroscopy are known, configured to measure parameters of an acoustic pressure wave created by rapid heating of the sampled area. Other glucose meters operate on measuring changes in the scattering and the polarization parameters of light caused by glucose molecules in the blood. Femtosecond pulse interferometry can be used to determine glucose concentration, by measuring the group refraction index of a glucose solution using a time delay of femtosecond order in a time-of-flight method. Optical coherence tomography can be used to measure and analyze the interference pattern between the coherently backscattered light from specific layers of tissues and a reference beam.

Optical techniques for monitoring and measuring various parameters of a sample, including blood related parameters have been described. Such techniques include:

U.S. Pat. No. 8,638,991 presents a method for imaging an object. The method comprises imaging a coherent speckle pattern propagating from an object, using an imaging system being focused on a plane displaced from the object.

U.S. Pat. No. 9,668,672 presents a system and method for use in monitoring one or more conditions of a subject's body. The system comprises a control unit which comprises an input port for receiving image data and data indicative of at least one external stimulation (external field) applied to a portion of the subject's body during collection of the image data therefrom, a memory utility, and a processor utility. The image data is indicative of a sequence of speckle patterns generated by the portion of the subject's body according to a certain sampling time pattern. The processor utility is configured and operable for carrying out the following: processing the image data utilizing the data indicative of the applied external field(s), said processing comprising determining a spatial correlation function between successive speckle patterns in the sequence, and determining a time varying spatial correlation function in the form of a time-varying function of at least one feature of the correlation function indicative of a change of the speckle pattern over time; selecting at least one parameter of the time-varying spatial correlation function, and applying to said at least one parameter one or more of the models to determine one or more corresponding body conditions; and generating output data indicative of said one or more corresponding body conditions.

GENERAL DESCRIPTION

As indicated above, optical monitoring techniques may provide non-invasive and efficient technique for monitoring parameters of a patient. Further, the use of coherent illumination and detection of variation in secondary speckle patterns generated in light returning, by reflectance and/or scattering, from an inspection region of the patient (herein referred to as speckle-based detection) can be used for measurement of such parameters. The efficiency and accuracy of speckle based monitoring of some parameters such as glucose concentration in blood may be increased utilizing external field stimulation such as magnetic external field. Generally, the presence of external magnetic field causes rotation of light polarization by interaction with glucose molecules due to Faraday Effect, thus allowing monitoring of glucose concentration.

When operating with alternating magnetic field, the alternating current (AC) variation and the magnetic field by itself may generate small mechanical vibrations adding undesired noise to the measurement. There is thus a need in the art for a novel technique enabling accurate measurement of selected parameters with increased signal to noise ratio thereby improving measurement accuracy in presence of AC magnetic field. The technique of the present invention utilizes pulsed illumination that is appropriately timed with operation of an external field stimulation to enable readout of data indicative of one or more desired parameters while reducing effects of undesired field generated vibrations.

More specifically, when alternating external stimulation is provided for affecting one or more properties of selected materials (or interaction of the materials with light) in the inspection region, undesired mechanical vibrations may also occur due to the changes in the stimulating field. The inventors of the present invention have found that mechanical vibration (acting as noise in this case) have certain rise time that is typically longer with respect to effects of the stimulation field on propertied of the selected materials, affecting the desired parameters to be measured. For example, vibrations due to AC magnetic field have rise-time that is longer than the time scale of Faraday Effect associated with interaction of light with glucose molecules under the stimulating magnetic field. Thus, the present technique provides for monitoring of an inspection region utilizing short illumination pulses, which are preferably timed with operation of the external field. This monitoring technique enable measurement of desired parameters affected by the field while filtering out mechanical vibrations occurring caused by the stimulation field but manifested at a later time, herein referred to as field related vibrations.

Utilizing the above described speckle-based detection, the present technique utilizes collection data on of temporal movements of a user's skin, and utilized this data for providing data about selected bio-parameters. Further, application of external stimulation field, such as magnetic field, allows monitoring of variations in the skins' movement in different conditions and enable separation between one or more selected parameters for monitoring. For example, application of magnetic field on media containing glucose molecules causes Faraday Effect, which in turn results in rotation of the plane of linearly polarized light when passing through the media. This changes the polarization state of the wavefront of light impinging on the region and returning therefrom, and results in corresponding changes of the speckle patterns formed in the returned light. The technique of the invention utilized temporal filtering of data collection for reducing effects of noise caused by application of external magnetic field. This allows greater accuracy in monitoring of bio-parameters such as glucose concentration.

Thus, according to a broad aspect of the present invention, there is provided a system for use in monitoring one or more parameters and/or conditions of a subject's body, the system comprising: an illumination unit configured for providing pulsed coherent illumination and directing said illumination onto an inspected region on said subject's body; a collection unit configured for collecting light returning from said inspection region and generate a plurality of data pieces associated with secondary speckle patterns in said light; an external field stimulation unit configured for selectively generating external field stimulation onto the subject's body; and a control unit configured and operable for operating said illumination unit said collection unit and said external field stimulation unit and for receiving said plurality of data pieces from said collection unit to thereby determine said one or more conditions of the subject's body.

The external field stimulation may generate a desired stimulation on at least a part of the subject's body and an undesired stimulation characterized as having certain rise-time. Generally the desired stimulation may be associated with magnetic field and/or acoustic stimulation of certain temporal length and selected amplitude, the stimulation may be repeating with a selected patterns. The illumination pulse may preferably be selected to be short with respect to rise-time of said undesired stimulation that may be resulting from operating of said external field stimulation unit.

According to some embodiments, the illumination pulses may be selected to be shorter with respect to rise-time of said undesired stimulation provides for eliminating, or at least significantly reducing a coupling between said desired and undesired stimulations.

Generally, the external field stimulation unit may be configured and operable for generating a time varying magnetic field at vicinity of the inspection region.

According to some embodiments, the control unit may comprise an operation timing module configured for timing operation of the external field stimulation unit, said illumination and said collection unit to enable monitoring with increased signal to noise ratio. It should be noted that generally the control unit may be configured as a computing unit comprising one or more processors, storage utility and input/output connection ports. The one or more processors may be operable in accordance with computer readable code providing instructions as described herein for operating of the one or more processors and communicating with additional units such as illumination, collection and stimulation unit when needed.

The operation timing module may be configured and operable to initiate operation of said external field stimulation unit to provide said external field stimulation applied in vicinity of the inspection region, initiate said illumination unit to generate one or more illumination pulse for illuminating said inspection region within selected stimulation time period and initiate said collection unit for collecting one or more image data pieces within duration of an illumination pulse of said one or more illumination pulses.

The operation timing module may be configured to operate said collection unit for collecting two or more image data pieces within duration of said selected stimulation time period, being within duration of one illumination pulse or a few illumination pulses repeating within the duration of single stimulation period.

According to some embodiments, the system may be configured such that said control unit comprises: a memory utility for storing one or more predetermined models indicative of a relation between one or more measurable parameters and one or more conditions of the subject's body; and a processor utility. The processor utility may be configured and operable for: processing input data received from the collection unit utilizing data about operation of said external field simulation unit, said processing comprising determining one or more spatial correlation functions between successive speckle patterns in the plurality of data pieces, and determining a time varying spatial correlation function in the form of a time-varying function of at least one feature of the correlation function, the time-varying spatial correlation function being indicative of a change of the speckle pattern over time; selecting at least one parameter of the time-varying spatial correlation function, and applying to said at least one parameter one or more of the models to determine one or more corresponding body conditions; and generating output data indicative of said one or more corresponding body conditions.

As indicated above, the control unit may be operable using one or more processors thereof in accordance with suitable computer readable instructions.

According to some embodiments, the system may be configured for monitoring glucose blood level of a subject. Such glucose level measurement may utilize alternating magnetic field stimulation and detection of Faraday Effect induced by the glucose molecules affecting polarization of returning light.

According to some other broad aspects of the invention, there is provided a method for monitoring one or more parameters of a subjects body, the method comprising: providing a predetermined stimulation at a vicinity of a region to be inspected of said subject's body for a selected stimulation time, providing pulsed coherent illumination onto said region and collecting two or more image data pieces associated with light returning from said region within at least a period of said stimulation time and processing said two or more image data pieces for determining data indicative of said one or more parameters, wherein said pulsed coherent illumination comprises one or more pulses being short with respect to rise-time of mechanical effects of said stimulation to thereby provide time-frequency filtering between effects of said stimulation.

Said providing a predetermined stimulation may comprise applying AC magnetic field in vicinity of said region, said one or more pulses of coherent illumination being characterized by pulses duration being shorter than rise-time of mechanical vibrations in response to said AC magnetic stimulation. The one or more parameters may comprises glucose blood level.

According to some embodiments, said processing may comprise determining one or more correlation function between speckle patterns in said two or more image data pieces and determining data about vibrations of said region in accordance with said one or more correlation functions.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
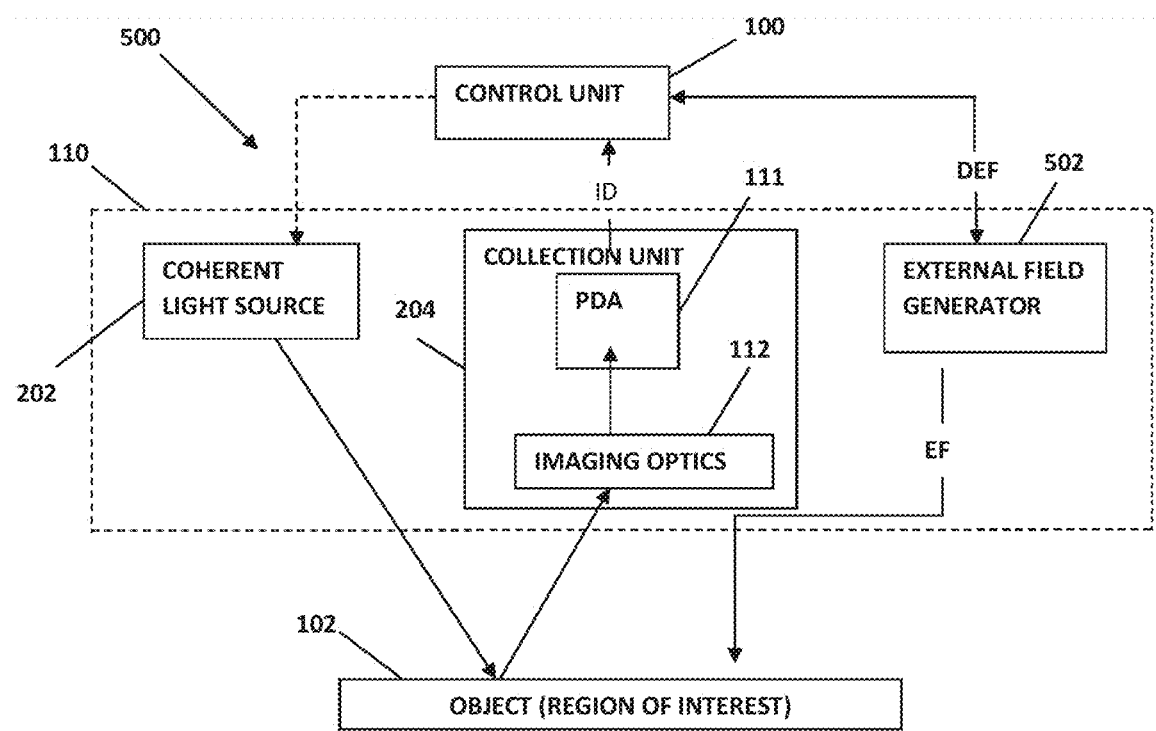
FIG. 1 schematically illustrates a system for improved monitoring according to some embodiments of the invention.

Reference is made to FIG. 1 schematically illustrating a measurement system 500 according to some configurations of the present invention. The system 500 is generally configured for monitoring one or more parameters of a sample, and typically parameters of a patient such as blood glucose concentration, alcohol content of blood and other such parameters. The system includes a measurement unit 110 and a control unit 100. The control unit 100 is configured for operating the measurement unit 110 and for receiving input data including measured data from the measurement unit 110 and apply processing thereto. The measurement unit 110 includes an illumination unit 202 configured to provide coherent illumination of selected wavelength range onto a selected inspection region, collection unit 204 configured for collecting light returning from the inspection region and generating one or more sequences of image data pieces associated with secondary speckle patterns formed in the returning light. The illumination unit 202 generally includes a coherent light source such a laser system and may also include an optical arrangement enabling direction of the illumination and desired spot size when needed. The collection unit 204 is exemplified herein by imaging optics 112 and pixel detector array (PDA) 111 arranged between them such that the imaging optics 112 provides imaging of an intermediate plane onto the detector array, and the collection unit 204 is defocused of the inspection region. The measurement system 110 may also include, or be associated with, an external field generator 502 configured for generating selected external stimulation onto the inspection region.

According to some configuration of the invention, the illumination unit 202 is configured for providing pulsed coherent illumination having selected pulse duration and directing the illumination onto an inspection region. In this connection, the inspection region may be a part on a subject's body (e.g. arm, leg, chest etc.). As indicated, the illumination unit 202 typically includes a laser light source and may be configured as CW light source with mechanical shutter or as a pulsed light source such as Q-switch laser unit or any other type of pulsed light source. The illumination unit 202 may be configured to provide illumination with specific selected polarization state and orientation. For example, the illumination unit may be configured to provide light with linear or elliptical polarization at desired angle with respect to surface of the inspection region, circular polarization or random polarization.

The collection unit 204 is configured for collecting light returning from the inspection region and operate at a selected sampling rate to generate image data pieces associated with secondary speckle pattern formed by interference of light components in the returning and scattered. As indicated above, the collection unit generally includes a detector array (PDA) 111 and a corresponding imaging optics 112 (e.g. one or more lenses) configured for defocused imaging of the inspection region onto the detector 111. More specifically, the imaging optics 112 is configured for collecting light returning from the inspection region with a selected field of view, and is located at a distance from the PDA 111 such that an image plane formed on the PDA 111 corresponds to an intermediate plane (intermediate object plane) shifted with respect to the inspection region. The intermediate plane may be located between the inspection region and the imaging optics or further from the inspection region. Thus the image data collected by the PDA corresponds to secondary speckle patterns formed by light interference while propagating away from the inspection region. The collection unit 204 is configured for generating sequences of image data pieces at a selected frame rate and for transmitting the generated image data pieces to the control unit 100 for processing. The collection unit 204 may also include one or more filtering elements such as chromatic filter, polarization filter etc. The use of filtering elements may provide for increased signal to noise ration as well as for separating speckle pattern data in having desire characteristics. Such as different polarization, from the background illumination.

The external field stimulation unit 502 is configured for generating a predetermined stimulation field EF (e.g. ultrasound, magnetic field etc.) onto the inspection region or its vicinity. For example, the external field stimulation unit 502 may be a magnetic field generator, such as a solenoid or coil, configured for generating alternating magnetic field in response to AC current transmitted therethrough, or an acoustic transducer operating at selected acoustic frequency range. Generally, according to some embodiments, the use of AC magnetic field may enable efficient detection of glucose levels in a patient's blood. This results from Faraday Effect exhibited by the glucose molecules in the blood and affects the optical field impinging on the inspection region in proportion to the glucose concentration in the blood. Alternatively, some other embodiments, may utilizes acoustic excitation or other electromagnetic effects of the inspection region providing detectable signal over mechanical vibrations that might be cause by the stimulation.

The control unit 100 may generally be configured, or include, a computing unit including one or more processor units, memory/storage unit as well as suitable input and output communication modules. The control unit may generally include stored data including computer readable instructions that when operated by one or more of the processor unit cause the processor units to perform desired actioned as described herein.

When operated according to the pre-stored instructions, the control unit 100 is configured and operable for providing operation commends and operating said measurement unit 110 to provide measured parameters with improved signal to noise ratio (SNR). To this end, the control unit 100 is configured for operating the illumination unit 202, the collection unit 204 and the external field stimulation unit 502, e.g. by transmitting data of external field DEF to the external field generator 502, according to a predetermined operational scheme designed for optimizing data collection. Such predetermined operational scheme may typically include selected timing illumination and image data collection with respect to start and end time of stimulation by the external field generator 502. Additionally, the control unit 100 is further configured and operable for receiving input data ID indicative of a plurality of data pieces from the collection unit 204 indicative of one or more conditions of the subject's body and for processing the received data and/or store the data and transmit is for further processing.

Generally, applying external stimulation, such as AC magnetic field, at a vicinity of an object to be inspected, e.g. patient's hand, may result in mechanical vibrations. For some types of measurements such vibrations introduce undesired noise over the desired signal. To this end, the control unit 100 is configured and operable for utilizing a predetermined operational scheme designed according to the present technique for increasing SNR in the collected data ID. This this end, the control unit 100 is configured for selectively operating the external field generator 502 for providing external stimulation (e.g. AC magnetic field) according to predetermined parameters DEF, such as frequency and amplitude, for a selected time duration herein referred to as stimulation time. During the operation time of the external field generator 502, the control unit 100 further operates the illumination unit 202 and collection unit 204 for illuminating the inspection region and collecting two or more image data pieces associated with speckle patterns in light returning from the inspection region 102 within a predetermined temporal window from the start of the stimulation time.

More specifically, the control unit 100 operates, by transmitting suitable operation commands, the illumination unit 202 for providing one or more illumination pulses directed at the inspection region. Additionally and simultaneously, the control unit operates the collection unit 204 for collecting two or more image data pieces within the duration of the illumination pulse(s). More specifically, in some configurations, the illumination unit may be configured or operated to generate a single illumination pulse having selected duration shorter than the stimulation time and the collection unit is operated for collecting two or more image data pieces within duration of the illumination pulse. In some other configurations, the illumination unit is configured and operated to provide one or more (generally two or more) illumination pulses such that the illumination pulses are within a selected portion of the stimulation time, and the collection unit is operated for collecting two or more image data pieces indicative of speckle patterns generated by light returning from the inspection region as a result of the illumination pulses. The former configuration is typically more suitable for use with collection unit 204 capable of collecting image data with short exposure time and the latter configuration may be used with collection unit 204 that might be limited with exposure time length such that the illumination pulses provide exposure limits for collection of image data pieces.

The image data collection scheme of the present technique enables collection of a plurality of two or more image data pieces within a selected temporal period from start point of the external stimulation. The selected temporal period for collection of image data pieces, within the stimulation time, may be determined in accordance with rise time of mechanical vibrations resulting directly from the stimulation field EF. As indicated above, such mechanical vibrations may act as undesired noise over desired signals such as variation in speckle patterns of light in selected polarization state, indicating level of Faraday Effect acting on certain molecules, e.g. glucose.

Figure 2:
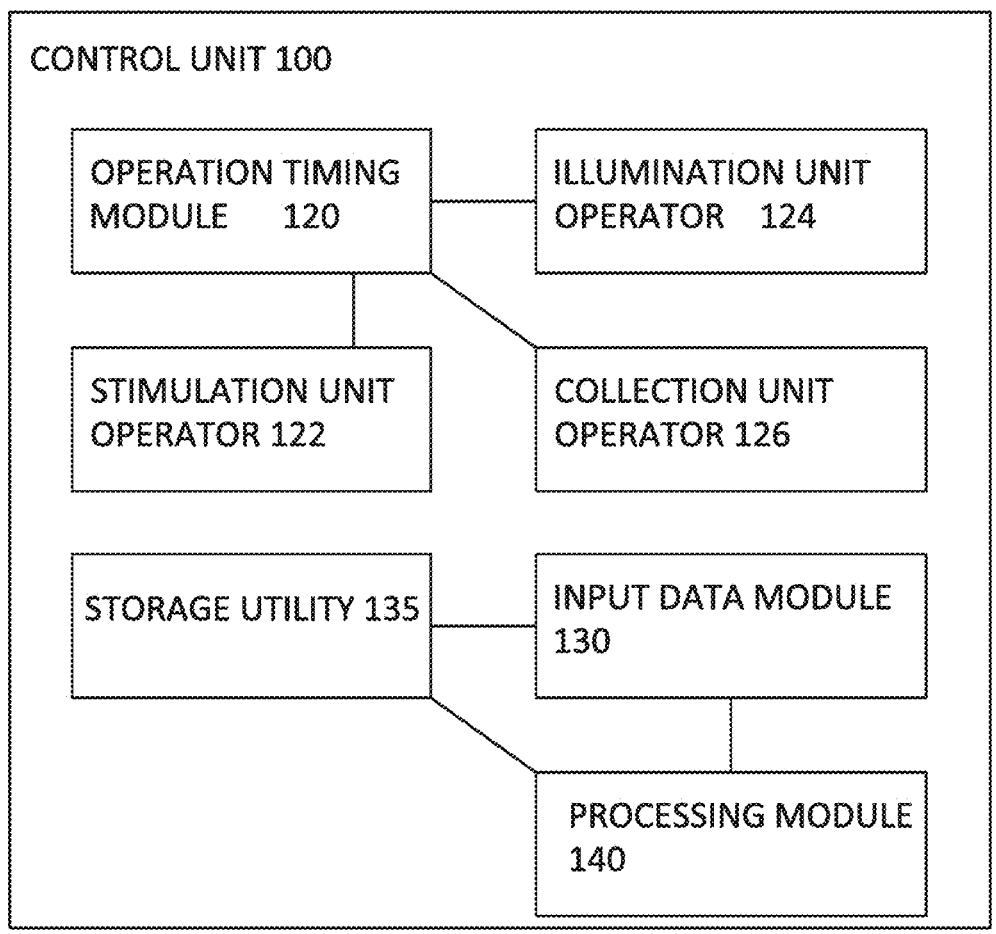
FIG. 2 illustrates a block diagram of a control unit configuration according to some embodiments of the invention.

As indicated above, the control unit 100 may generally be configured as a computing unit, or as electronic control unit, and include an operation timing module configured and operable for appropriately timing operation of the stimulation unit 502, illumination unit 202 and collection unit 204 in accordance with the selected operational scheme. In this connection, reference is made to FIG. 2 schematically illustrating main modules of the control unit 100. As shown, the control unit may include an operation timing module 120 (e.g. internal clock and timer module) configured and operable for timing operation of the different units of the system 500. The operation timing module 120 is connected to stimulation unit operator 122, illumination unit operator 124 and collection unit operator 126 and configured for timing operation of the units by transmitting corresponding signals vie the respective operator modules. As also shown, the control unit 100 may include an input data module 130, processing module 140 and storage utility 135, for use receiving and processing collected data. Generally the different modules may be software and/or hardware modules and may be associated with one or more processors of the control unit 100.

Also, as indicated above, the control unit 100 may include one or more storage utilities and input and output communication ports for network communication as well as for transmitting operational command to the illumination, collection and stimulation units (202, 204 and 502). Further, the control unit may also include user interface such as screen and operation buttons for communication with an operator and providing data on operation and determined measurement results.

Generally, the operation timing module 120 is configured to transmit operation signals to the stimulation unit 502, e.g. via the stimulation unit operator 122, for providing stimulation for a selected time period. Within the selected time period, the operation timing module 120 operates the illumination unit operator 124 to transmit operation signals to the illumination unit 202 for providing one or more pulses of illumination and operates the collection unit operator 126 to command the collection unit 204 for collecting two or more image data pieces. As indicated above, the illumination unit operator 122 may be configured, according to some embodiments, to cause the illumination unit 202 to provide a single pulse of illumination together with stimulation time, associated with operation of the external field generator 502, while the collection unit 204 is operated for collecting two or more image data pieces within duration of the illumination pulse. Alternatively, the illumination unit operator 122 may be configured to operate the illumination unit 202 to provide a series of two or more pulses starting with operation of the field generator 502, while the collection unit 204 is operated, by the collection unit operator 124, for collecting a corresponding series of two or more image data pieces associated with the illumination pulses. It should be noted that the use of pulsed illumination of selectively short pulses enables collecting image data associated with short time window (shorter than integration time of the PDA of the collection unit), such that the collection unit may be configured with integration time that is longer than duration of the illumination pulses.

Figure 3:
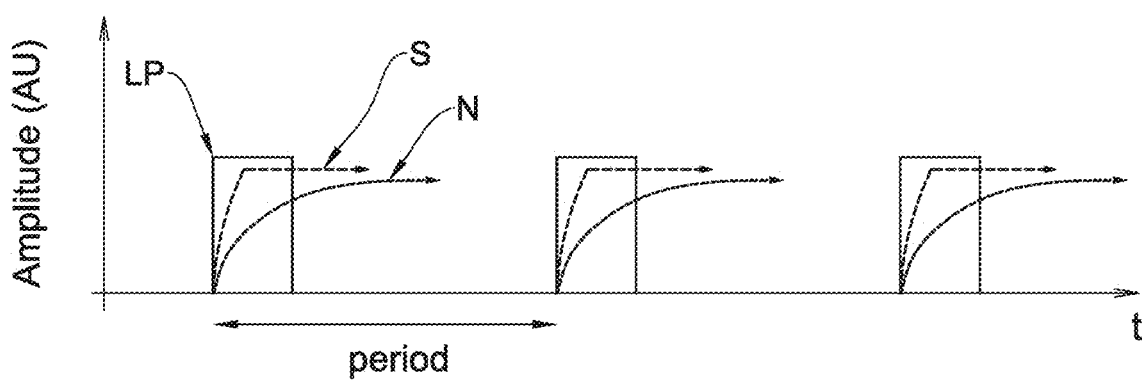
FIG. 3 exemplifies a technique for increasing of signal to noise ratio according to the technique of the invention.

Reference is made to FIG. 3 exemplifying the present technique for increasing of signal to noise ratio. FIG. 3 shows a graph indicating operation of a sequence of illumination pulses LP, which are operated simultaneously with the external stimulation signal, (e.g. AC magnetic field), expected signals S to be measured and estimated noise N resulting e.g. from mechanical vibrations associated with AC magnetic field. In the exemplary embodiment of glucose concentration measurement, AC magnetic field may be preferably used. The AC magnetic field applied on the glucose molecules causes Faraday rotation to light interacting with the molecules which results in polarization rotation. However, applying AC magnetic field on the sample may also result in small vibrations at a similar frequency as that of the magnetic field. These vibrations might be sensed together with the vibrations caused by blood flow (for the case of glucose monitoring) or any other desired signals, resulting in addition of noise. The inventors of the present invention have found that the mechanical vibrations N caused by the external stimulation (and in particular by AC magnetic field) have rise-time that is longer than that of the Faraday effect (in the case of magnetic field) measured on top of the vibrations associated with blood flow. Thus, the use of pulsating illumination LP combined with periodic stimulation enables detection of the desired signal S within a short time window where the mechanical vibrations are relatively lower. The collected data indicative of speckle patterns is collected by the collection unit, as two or more image data pieces, within the time window of illumination (being a single illumination pulse as exemplified in FIG. 3 or two or more illumination pulses). This provides temporal filtering of the desired signal over undesired noise that may be caused by the stimulation. It should also be noted that, as shown in FIG. 3, the technique may include repetitive measurement with a predetermined repetition rate for increasing measurement accuracy, or a single measurement in accordance with desired accuracy and type of the measured signal.

Thus, the technique of the invention provides for monitoring of parameters, such as blood glucose concentration, in presence of external stimulation filed while allowing increased single to noise ratio. The present technique utilizes temporal filtering, differentiating between desired signal and noise, using pulsed illumination allowing collection of the desired signal at selected time windows. Those skilled in the art will readily appreciate that various modifications and changes can be applied to the embodiments of the invention as hereinbefore described without departing from its scope defined in and by the appended claims.

The invention claimed is:

1. A system for use in monitoring one or more parameters of a subject's body, the system comprising:
an illuminator configured to provide pulsed coherent illumination and directing said illumination onto an inspection region on said subject's body;
a light collector configured to collect light returning from said inspection region and generate a plurality of image data pieces associated with secondary speckle patterns in said light;
an external field stimulator configured to selectively generate external field stimulation applied onto the subject's body, wherein said external field stimulator is capable of generating a desired stimulation on at least a part of the subject's body and an undesired stimulation having certain rise-time, said pulsed coherent illumination comprising one or more illumination pulses selected to be short with respect to said certain rise-time of said undesired stimulation;
and a processor configured and operable to operate said illuminator, said light collector, and said external field stimulator and to receive and process said plurality of data pieces from said light collector to thereby determine one or more of the following conditions of the subject's body: glucose level, oxygen level, alcohol level.

2. A system for use in monitoring one or more parameters of a subject's body, the system comprising:
an illuminator configured to provide pulsed coherent illumination and directing said illumination onto an inspection region on said subject's body;
a light collector configured to collect light returning from said inspection region and generate a plurality of image data pieces associated with secondary speckle patterns in said light;
an external field stimulator configured to selectively generate external field stimulation applied onto the subject's body; and
a processor configured and operable to operate said illuminator, said light collector, and said external field stimulator and to receive and process said plurality of data pieces from said light collector to thereby determine one or more of the following conditions of the subject's body: glucose concentration, oxygen level, alcohol level,
wherein said processor comprises an operation timing module configured for timing operation of the external field stimulator, the illuminator, and the light collector to enable monitoring with increased signal to noise ratio, said operation timing module being configured and operable to initiate operation of said external field stimulator to provide said external field stimulation applied in vicinity of the inspection region, initiate said illuminator to generate one or more illumination pulses for illuminating said inspection region within selected stimulation time period and initiate said light collector for collecting one or more image data pieces within duration of said one or more illumination pulses, wherein said operation timing module is configured to operate said light collector for collecting two or more image data pieces within duration of said selected stimulation time period.

3. The system of claim 1, wherein said illumination pulses being shorter with respect to rise-time of said undesired stimulation provides for eliminating, or at least significantly reducing a coupling between said desired and undesired stimulations.

4. The system of claim 1, wherein said external field stimulator is configured and operable for generating a time varying magnetic field at vicinity of the inspection region.

5. The system of claim 1, wherein said processor comprises an operation timing module configured for timing operation of the external field stimulator, said illuminator, and said light collector to enable monitoring with increased signal to noise ratio.

6. The system of claim 5, wherein said operation timing module is configured and operable to initiate operation of said external field stimulator to provide said external field stimulation applied in vicinity of the inspection region, initiate said illuminator to generate one or more illumination pulses for illuminating said inspection region within selected stimulation time period and initiate said light collector for collecting one or more image data pieces within duration of said one or more illumination pulses.

7. The system of claim 6, wherein said operation timing module is configured to operate said light collector for collecting two or more image data pieces within duration of said selected stimulation time period.

8. The system of claim 1, wherein said processor comprises:
a memory utility for storing one or more predetermined models indicative of a relation between one or more measurable parameters and one or more conditions of the subject's body;
and a processor utility configured and operable for:
processing input data received from the light collector utilizing data about operation of said external field simulator, said processing comprising determining one or more spatial correlation functions between successive speckle patterns in the plurality of data pieces, and determining at least one time varying spatial correlation function in the form of a time-varying function of at least one feature of the correlation function, the time-varying spatial correlation function being indicative of a change of the speckle pattern over time;
i) selecting at least one parameter of the time-varying spatial correlation function, and applying to said at least one parameter one or more of the models to determine one or more corresponding body conditions; and
ii) generating output data indicative of said one or more corresponding body conditions.

9. The system of claim 1, configured for monitoring glucose blood level of a subject.

10. A method for monitoring one or more parameters of a subjects body, the method comprising: providing a predetermined stimulation at a vicinity of a region to be inspected of said subject's body for a selected stimulation time, providing pulsed coherent illumination onto said region and collecting two or more image data pieces associated with light returning from said region within at least a period of said stimulation time and processing said two or more image data pieces for determining data indicative of said one or more parameters, wherein said pulsed coherent illumination comprises one or more pulses being short with respect to rise-time of mechanical effects of said stimulation to thereby provide time-frequency filtering between effects of said stimulation, wherein said one or more parameters of the subject's body comprises one or more of the following: glucose level, oxygen level, alcohol level.

11. The method of claim 10, wherein said providing a predetermined stimulation comprises applying AC magnetic field in vicinity of said region, said one or more pulses of coherent illumination being characterized by pulse duration being shorter than rise-time of mechanical vibrations in response to said AC magnetic stimulation.

12. The method of claim 10, wherein said one or more parameters comprises glucose blood level.

13. The method of claim 10, wherein said processing comprises determining one or more correlation function between speckle patterns in said two or more image data pieces and determining data about vibrations of said region in accordance with said one or more correlation functions.

14. The system of claim 2, wherein said external field stimulation generates a desired stimulation on at least a part of the subject's body and an undesired stimulation having certain rise-time, said pulsed coherent illumination comprising one or more illumination pulses selected to be short with respect to said certain rise-time of said undesired stimulation.

* * * * *